US008722568B2

(12) United States Patent
Popp et al.

(10) Patent No.: US 8,722,568 B2
(45) Date of Patent: May 13, 2014

(54) SUPPORT PROPERTIES OF SILICA SUPPORTED CATALYSTS AND THEIR USE IN OLEFIN METATHESIS (75) Inventors: Kristoffer E. Popp, Chicago, IL (US); Mark A. Krawczyk, Chicago, IL (US); Christopher P. Nicholas, Evanston, IL (US); Jennifer F. Abrahamian, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/550,649

(22) Filed: Jul. 17, 2012

(65) Prior Publication Data
US 2012/0283090 A1 Nov. 8, 2012

Related U.S. Application Data (62) Division of application No. 12/701,503, filed on Feb. 5, 2010, now Pat. No. 8,324,440.

(51) Int. Cl.
*B01J 21/00* (2006.01)
*B01J 23/10* (2006.01)
*B01J 23/00* (2006.01)

(52) U.S. Cl.
USPC .......................................... 502/254; 502/305

(58) Field of Classification Search
USPC .......... 585/310, 324, 643, 646; 502/232, 233, 502/254, 305
See application file for complete search history.

(56) References Cited

U.S. PATENT DOCUMENTS

2006/0070915 A1* 4/2006 Euzen et al. ............... 208/111.3
2006/0293548 A1* 12/2006 Spamer et al. ............... 585/643
2008/0300434 A1* 12/2008 Cortright et al. ............... 585/1

OTHER PUBLICATIONS

Wang et al., "Effect of support nature on WO3/SiO2 structure and butene-1 metathesis" Applied Catalysis A: General 250 (2003) 25-37.*
Zhao et al., "Effect of tungsten oxide loading on metathesis activity of ethene and 2-butene over WO3/SiO2 catalysts," Transition Met Chem (2009) 34:621-627, Published Online Jun. 23, 2009.*
Kim et al., "Preparation and characterization of WO3/SiO2 catalysts," Catalysis Letters 33 (1995) 209-215.*
Lokhat et al., "Gas-phase metathesis of 1-hexene over a WO3/SiO2 catalyst: Search for optimal reaction conditions", Applied Catalysis A: General 351 (2008) 137-147.*
Huang et al, "The influence of preparation procedures and tungsten loading on the metathesis activity of ethene and 2-butene over supported WO3 catalysts," Journal of Molecular Catalysis A: Chemcial 267 (2007) 224-233.*
Yang et al., "Novel efficient and green approach to the synthesis of glutaraldehyde over highly active W-doped SBA-15 catalyst," Journal of Catalysis 229 (2005) 259-263.*

* cited by examiner

Primary Examiner — Anthony J Zimmer
(74) Attorney, Agent, or Firm — Arthur E. Gooding (57) ABSTRACT Silica supports having a surface area from about 250 m²/g to about 600 m²/g and an average pore diameter from about 45 Å to about 170 Å, used for supported tungsten catalysts, improves the activity of the resulting catalyst (i.e., its conversion level at a given temperature) for the metathesis of olefins, without compromising its selectivity to the desired conversion product(s). Exemplary catalysts and processes include those for the production of valuable light olefins such as propylene from a hydrocarbon feedstock comprising ethylene and butylene.

5 Claims, 4 Drawing Sheets

SUPPORT PROPERTIES OF SILICA SUPPORTED CATALYSTS AND THEIR USE IN OLEFIN METATHESIS

CROSS-REFERENCE TO RELATED APPLICATION

This application is a Division of U.S. application Ser. No. 12/701,503 filed on Feb. 5, 2010, the entire contents of which are hereby incorporated by reference

FIELD OF THE INVENTION

The invention relates to catalysts and processes for the metathesis of olefins, for example in the production of propylene from olefin feedstocks comprising ethylene and butylene. A representative catalyst comprises tungsten (e.g., present as tungsten oxide ($WO_3$)) on a support comprising silica having a surface area from about 250 $m^2/g$ to about 600 $m^2/g$ and an average pore diameter from about 45 Å to about 170 Å.

DESCRIPTION OF RELATED ART

Propylene demand in the petrochemical industry has grown substantially, largely due to its use as a precursor in the production of polypropylene for packaging materials and other commercial products. Other downstream uses of propylene include the manufacture of acrylonitrile, acrylic acid, acrolein, propylene oxide and glycols, plasticizer oxo alcohols, cumene, isopropyl alcohol, and acetone. Currently, the majority of propylene is produced during the steam cracking or pyrolysis of hydrocarbon feedstocks such as natural gas, petroleum liquids, and carbonaceous materials (e.g., coal, recycled plastics, and organic materials). The major product of steam cracking, however, is generally ethylene and not propylene.

Steam cracking involves a very complex combination of reaction and gas recovery systems. Feedstock is charged to a thermal cracking zone in the presence of steam at effective conditions to produce a pyrolysis reactor effluent gas mixture. The mixture is then stabilized and separated into purified components through a sequence of cryogenic and conventional fractionation steps. Generally, the product ethylene is recovered as a low boiling fraction, such as an overhead stream, from an ethylene/ethane splitter column requiring a large number of theoretical stages due to the similar relative volatilities of the ethylene and ethane being separated. Ethylene and propylene yields from steam cracking and other processes may be improved using known methods for the metathesis or disproportionation of $C_4$ and heavier olefins, in combination with a cracking step in the presence of a zeolitic catalyst, as described, for example, in U.S. Pat. Nos. 5,026,935 and 5,026,936. The cracking of olefins in hydrocarbon feedstocks, to produce these lighter olefins from $C_4$ mixtures obtained in refineries and steam cracking units, is described in U.S. Pat. Nos. 6,858,133; 7,087,155; and 7,375,257.

Steam cracking, whether or not combined with conventional metathesis and/or olefin cracking steps, does not yield sufficient propylene to satisfy worldwide demand. Other significant sources of propylene are therefore required. These sources include byproducts of fluid catalytic cracking (FCC) and resid fluid catalytic cracking (RFCC), normally targeting gasoline production. FCC is described, for example, in U.S. Pat. No. 4,288,688 and elsewhere. A mixed, olefinic $C_3/C_4$ byproduct stream of FCC may be purified in propylene to polymer grade specifications by the separation of $C_4$ hydrocarbons, propane, ethane, and other compounds.

Much of the current propylene production is therefore not "on purpose," but as a byproduct of ethylene and gasoline production. This leads to difficulties in coupling propylene production capacity with its demand in the marketplace. Moreover, much of the new steam cracking capacity will be based on using ethane as a feedstock, which typically produces only ethylene as a final product. Although some hydrocarbons heavier than ethylene are present, they are generally not produced in quantities sufficient to allow for their recovery in an economical manner. In view of the current high growth rate of propylene demand, this reduced quantity of co-produced propylene from steam cracking will only serve to accelerate the increase in propylene demand and value in the marketplace.

A dedicated route to light olefins including propylene is paraffin dehydrogenation, as described in U.S. Pat. No. 3,978,150 and elsewhere. However, the significant capital cost of a propane dehydrogenation plant is normally justified only in cases of large-scale propylene production units (e.g., typically 250,000 metric tons per year or more). The substantial supply of propane feedstock required to maintain this capacity is typically available from propane-rich liquefied petroleum gas (LPG) streams from gas plant sources. Other processes for the targeted production of light olefins involve high severity catalytic cracking of naphtha and other hydrocarbon fractions. A catalytic naphtha cracking process of commercial importance is described in U.S. Pat. No. 6,867,341.

More recently, the desire for propylene and other light olefins from alternative, non-petroleum based feeds has led to the use of oxygenates such as alcohols and, more particularly, methanol, ethanol, and higher alcohols or their derivatives. Methanol, in particular, is useful in a methanol-to-olefin (MTO) conversion process described, for example, in U.S. Pat. No. 5,914,433. The yield of light olefins from such processes may be improved using olefin cracking to convert some or all of the $C_4^+$ product of MTO in an olefin cracking reactor, as described in U.S. Pat. No. 7,268,265. An oxygenate to light olefins conversion process in which the yield of propylene is increased through the use of dimerization of ethylene and metathesis of ethylene and butylene, both products of the conversion process, is described in U.S. Pat. No. 7,586,018.

Despite the use of various dedicated and non-dedicated routes for generating light olefins industrially, the demand for propylene continues to outpace the capacity of such conventional processes. Moreover, further demand growth for propylene is expected. A need therefore exists for cost-effective methods that can increase propylene yields from both existing refinery hydrocarbons based on crude oil as well as non-petroleum derived feed sources.

SUMMARY OF THE INVENTION

The invention is associated with the discovery of catalysts and processes for olefin metathesis, including those for the production of valuable light olefins such as propylene. More particularly, it has been found that a combination of properties of silica, and in particular a surface area and an average pore diameter (or pore size) within certain ranges, when used for supported tungsten oxide catalysts, effectively improves the activity of the resulting catalyst (i.e., its conversion level at a given temperature) for the metathesis of olefins, without significantly compromising its selectivity to the desired conversion product(s). In fact, the use of silica supports having the properties described herein can surprisingly provide increases in both conversion and selectivity under favorable olefin metathesis conditions, contrary to normal expectations that greater conversion levels are obtained at the expense of a loss in selectivity. The ranges of surface area and average pore diameter characteristics of silica, used in the tungsten oxide catalysts found to exhibit these performance advantages, are both selected from much broader ranges representative of the wide variety of silicas (e.g., both amorphous and crystalline) available.

Without being bound by theory, it is thought that these experimentally observed benefits result from a synergistic combination of surface area and average pore diameter, when within the ranges discussed herein, that provides favorable effects in terms of both reaction kinetics and molecular diffusion. These effects are believed to contribute to the demonstrated high yield (the product of conversion and selectivity) of the desired product(s). Increased olefin metathesis catalyst activity may be exploited commercially by reducing the requirement to heat the olefin-containing hydrocarbon feedstock, prior to its contact with the catalyst at the inlet of the olefin metathesis reaction zone. Alternatively, increased product yield may be obtained at a given reactor temperature. It will be recognized that cost advantages, associated with decreased energy requirements and/or greater product value, result in either case. In view of the current demand for propylene, it will also be appreciated that even a slight improvement in product yield, on the order of only a few percent, can result in substantial economic advantages, on the order of several million dollars per year in increased product value, for a typical petrochemical producer. The improved value of the product slate is accompanied by a reduction in downstream separation requirements for removing non-selective reaction products (e.g., $C_5^+$ olefins), and also a reduction in equipment and utilities required for the recycle of unconverted olefin reactants.

Accordingly, embodiments of the invention relate to olefin metathesis processes comprising contacting a hydrocarbon feedstock with a catalyst comprising tungsten disposed on a support comprising silica having a surface area from about 250 $m^2/g$ to about 600 $m^2/g$ and an average pore diameter from about 45 Å to about 170 Å. The hydrocarbon feedstock comprises olefins including a first olefin (e.g., ethylene) and a second olefin (e.g., butylene) having a carbon number of at least two greater than that of the first olefin, to produce a third olefin (e.g., propylene) having a carbon number intermediate to the first and second olefins. More particular embodiments of the invention relate to processes for producing propylene from the metathesis of ethylene and butylene. The processes comprise contacting a hydrocarbon feedstock comprising predominantly ethylene and butylene at an ethylene:butylene molar ratio from about 0.5:1 to about 3:1 with a catalyst comprising tungsten disposed on a silica support having a having a surface area from about 250 $m^2/g$ to about 600 $m^2/g$ and an average pore diameter from about 45 Å to about 170 Å. According to any of the above embodiments, the catalyst may comprise tungsten in an amount from about 1% to about 10% by weight and the support may have a silica to alumina ($SiO_2/Al_2O_3$) molar ratio of at least about 1000. A representative conversion level of the ethylene and the butylene is from about 30% to about 80%, based on carbon. Also, a representative selectivity, at which the ethylene and the butylene are converted to propylene, is at least about 50%, based on carbon.

Further embodiments of the invention relate to catalysts (e.g., for olefin metathesis) comprising tungsten (e.g., as tungsten oxide) disposed on a support comprising silica having a surface area from about 250 $m^2/g$ to about 600 $m^2/g$ and an average pore diameter from about 45 Å to about 170 Å.

Yet further embodiments of the invention relate to methods for preparing catalysts (e.g., for olefin metathesis) comprising tungsten oxide disposed on a support comprising silica. The methods comprise (a) impregnating a support comprising silica having a surface area from about 250 $m^2/g$ to about 600 $m^2/g$ and an average pore diameter from about 45 Å to about 170 Å with a tungsten compound to provide a tungsten impregnated silica support, and (b) calcining the tungsten impregnated silica support to provide the catalyst.

These and other aspects and embodiments associated with the present invention are apparent from the following Detailed Description.

DETAILED DESCRIPTION

As discussed above, the present invention is associated with catalytic olefin metathesis (or disproportionation) processes in which a hydrocarbon feedstock is contacted, in a metathesis reactor or reaction zone, with a catalyst comprising tungsten disposed on a support comprising silica having properties found to be particularly advantageous, including a surface area from about 250 $m^2/g$ to about 600 $m^2/g$ and an average pore diameter from about 45 Å to about 170 Å. The hydrocarbon feedstock refers to the total, combined feed, including any recycle hydrocarbon streams, to the catalyst in the metathesis reactor or reaction zone, but not including any non-hydrocarbon gaseous diluents (e.g., nitrogen), which may be added along with the feed according to some embodiments. The hydrocarbon feedstock may, but does not necessarily, comprise only hydrocarbons. The hydrocarbon feedstock generally comprises predominantly (i.e., at least 50% by weight) hydrocarbons, typically comprises at least about 80% (e.g., from about 80% to about 100%) hydrocarbons, and often comprises at least about 90% (e.g., from about 90% to about 100% by weight) hydrocarbons.

Also, in olefin metathesis processes according to the present invention, the hydrocarbons contained in the hydrocarbon feedstock are generally predominantly (i.e., at least 50% by weight, such as from about 60% to about 100% by weight) olefins, typically they comprise at least about 75% (e.g., from about 75% to about 100%) by weight olefins, and often they comprise at least about 85% (e.g., from about 85% to about 100% or from about 95% to about 100%) by weight olefins. In other embodiments, these amounts of olefins are representative of the total olefin percentages in the hydrocarbon feedstock itself, rather than the olefin percentages of the hydrocarbons in the hydrocarbon feedstock. In yet further embodiments, these amounts of olefins are representative of the total percentage of two particular olefins in the hydrocarbon feedstock, having differing carbon numbers, which can combine in the metathesis reactor or reaction zone to produce a third olefin having an intermediate carbon number (i.e., having a carbon number intermediate to that of (i) a first olefin (or first olefin reactant) and (ii) a second olefin (or second olefin reactant) having a carbon number of at least two greater than that of the first olefin). In general, the two olefins are present in the hydrocarbon feedstock to the metathesis reactor in a molar ratio of the first olefin to the second olefin from about 0.2:1 to about 10:1, typically from about 0.5:1 to about 3:1, and often from about 1:1 to about 2:1.

In an exemplary embodiment, the two olefins (first and second olefins) of interest are ethylene (having two carbons) and butylene (having four carbons), which combine in the metathesis reactor or reaction zone to produce desired propylene (having three carbons). The term "butylene" is meant to encompass the various isomers of the $C_4$ olefin butene, namely butene-1, cis-butene-2, trans-butene-2, and isobutene. In the case of metathesis reactions involving butylene, it is preferred that the butylene comprises predominantly (i.e., greater than about 50% by weight) butene-2 (both cis and trans isomers) and typically comprises at least about 85% (e.g., from about 85% to about 100%) butene-2, as butene-2 is generally more selectively converted, relative to butene-1 and isobutylene, to the desired product (e.g., propylene) in the metathesis reactor or reaction zone. In some cases, it may be desirable to increase the butene-2 content of butylene, for example to achieve these ranges, by subjecting butylene to isomerization to convert butene-1 and isobutylene, contained in the butylene, to additional butene-2. The isomerization may be performed in a reactor that is separate from the reactor used for olefin metathesis. Alternatively, the isomerization may be performed in an isomerization reaction zone in the same reactor that contains an olefin metathesis reaction zone, for example by incorporating an isomerization catalyst upstream of the olefin metathesis catalyst or even by combining the two catalysts in a single catalyst bed. Suitable catalysts for carrying out the desired isomerization to increase the content of butene-2 in the butylene are known in the art and include, for example, magnesium oxide containing isomerization catalysts as described in U.S. Pat. No. 4,217,244.

As discussed above, the olefins may be derived from petroleum or non-petroleum sources. Crude oil refining operations yielding olefins, and particularly butylene, include hydrocarbon cracking processes carried out in the substantial absence of hydrogen, such as fluid catalytic cracking (FCC) and resid catalytic cracking (RCC). Olefins such as ethylene and butylene are recovered in enriched concentrations from known separations, including fractionation, of the total reactor effluents from these processes. Another significant source of ethylene is steam cracking, as discussed above. A stream enriched in ethylene is generally recovered from an ethylene/ethane splitter as a low boiling fraction, relative to the feed to the splitter, which fractionates at least some of the total effluent from the steam cracker and/or other ethylene containing streams. In the case of olefins derived from non-petroleum sources, both the ethylene and butylene, for example, may be obtained as products of an oxygenate to olefins conversion process, and particularly a methanol to light olefins conversion process. Such processes are known in the art, as discussed above, and optionally include additional conversion steps to increase the butylene yield such as by dimerization of ethylene and/or selective saturation of butadiene, as described in U.S. Pat. No. 7,568,018. According to various embodiments of the invention, therefore, at least a portion of the ethylene in the hydrocarbon feedstock is obtained from a low boiling fraction of an ethylene/ethane splitter and/or at least a portion of the butylene is obtained from an oxygenate to olefins conversion process.

In representative olefin metathesis processes, with an exemplary process being the metathesis of ethylene and butylene for the production of propylene, catalysts comprising tungsten (e.g., as tungsten oxide prior to use in olefin metathesis) supported on silica having the advantageous properties described herein, may be used to achieve economically favorable product yields under commercial process conditions. With respect to the first and second olefins (e.g., ethylene and butylene) that undergo metathesis, the conversion level, based on the amount of carbon in these reactants that are converted to the desired product and byproducts (e.g., propylene and heavier, $C_5^+$ hydrocarbons), is generally from about 40% to about 80% by weight, and typically from about 50% to about 75% by weight. Significantly higher conversion levels, on a "per pass" basis through the metathesis reactor or reaction zone, are normally difficult to achieve due to equilibrium limitations, with the maximum conversion depending on the specific olefin reactants and their concentrations as well as process conditions (e.g., temperature).

In one or more separations (e.g., fractionation) downstream of the metathesis reactor or reaction zone, the desired product (e.g., propylene) may be recovered in substantially pure form by removing and recovering unconverted olefins (e.g., ethylene and butylene) as well as reaction byproducts (e.g., $C_5^+$ hydrocarbons including olefin oligomers and alkylbenzenes). Recycling of the unconverted olefin reactants back to the metathesis reactor or reaction zone may often be desirable for achieving complete or substantially complete overall conversion, or at least significantly higher overall conversion (e.g., from about 80% to about 100% by weight, or from about 95% to about 100% by weight) than the equilibrium-limited per pass conversion levels discussed above. The downstream separation(s) are normally carried out to achieve a high purity of the desired product, particularly in the case of propylene. For example, the propylene product typically has a purity of at least about 99% by volume, and often at least about 99.5% by volume to meet polymer grade specifications. According to other embodiments, the propylene purity may be lower, depending on the end use of this product. For example, a purity of at least about 95% (e.g., in the range from about 95% to about 99%) by volume may be acceptable for a non-polymer technology such as acrylonitrile production, or otherwise for polypropylene production processes that can accommodate a lower purity propylene.

At the per pass conversion levels discussed above, the selectivity of the converted feedstock olefin components (e.g., ethylene and propylene) to the desired olefins) (e.g., propylene) having an intermediate carbon number is generally at least about 75% (e.g., in the range from about 75% to about 100%) by weight, typically at least about 80% (e.g., in the range from about 80% to about 99%) by weight, and often at least about 90% (e.g., in the range from about 90% to about 97%) by weight, based on the amount of carbon in the converted products. The per pass yield of the desired olefin(s) is the product of the selectivity to this/these products) and the per pass conversion, which may be within the ranges discussed above. The overall yield, using separation and recycle of the unconverted olefin reactants as discussed above, can approach this/these product selectivity/selectivities, as essentially complete conversion is obtained (minus some purge and solution losses of feedstock and product(s), as well as losses due to downstream separation inefficiencies).

The conversion and selectivity values discussed above are achieved by contacting the hydrocarbon feedstock described above, either continuously or batchwise, with a catalyst as described herein comprising tungsten disposed on a support comprising silica having a surface area from about 250 m$^2$/g to about 600 m$^2$/g and an average pore diameter from about 45 Å to about 170 Å. Generally, the contacting is performed with the hydrocarbon feedstock being passed continuously through a fixed bed of the catalyst in an olefin metathesis reactor or reaction zone. For example, a swing bed system may be utilized, in which the flowing hydrocarbon feedstock is periodically re-routed to (i) bypass a bed of catalyst that has become spent or deactivated and (ii) subsequently contact a bed of fresh catalyst. A number of other suitable systems for carrying out the hydrocarbon/feedstock contacting are known in the art, with the optimal choice depending on the particular feedstock, rate of catalyst deactivation, and other factors. Such systems include moving bed systems (e.g., counter-current flow systems, radial flow systems, etc.) and fluidized bed systems, any of which may be integrated with continuous catalyst regeneration, as is known in the art.

As discussed above, the use of silica having a surface area from about 250 m$^2$/g to about 600 m$^2$/g and an average pore diameter from about 45 Å to about 170 Å, as a support for the olefin metathesis catalyst comprising tungsten, results in significant performance benefits in terms of both catalyst activity and selectivity, and consequently the yield of the desired product (e.g., propylene) achieved at a given reaction temperature. Surprisingly, therefore, the increase in conversion level does not result in a loss in selectivity, as is normally observed, for example, when reaction severity is increased (e.g., by raising temperature, increasing residence time, and/or increasing reactant concentrations). Representative conditions for olefin metathesis (i.e., conditions for contacting the hydrocarbon feedstock and catalyst in the olefin metathesis reactor or reaction zone), in which the above conversion and selectivity levels may be obtained, include a temperature from about 300° C. (572° F.) to about 600° C. (1112° F.), and often from about 400° C. (752° F.) to about 500° C. (932° F.); a pressure from about 10 barg (145 psig) to about 80 barg (1160 psig), and often from about 15 barg (218 psig) to about 45 barg (653 psig); and a weight hourly space velocity (WHSV) from about 1 hr$^{-1}$ to about 10 hr$^{-1}$. As is understood in the art, the WHSV is the weight flow of the hydrocarbon feedstock divided by the weight of the catalyst bed and represents the equivalent catalyst bed weights of feed processed every hour. The WHSV is related to the inverse of the reactor residence time. Under the olefin metathesis conditions described above, the hydrocarbon feedstock is normally in the vapor phase in the olefin metathesis reactor or reaction zone, but it may also be in the liquid phase, for example, in the case of heavier (higher carbon number) olefin feedstocks.

Importantly, the tungsten catalysts according to embodiments of the invention and providing the significant benefits, as discussed herein, in olefin metathesis comprise a support comprising silica having the advantageous properties described above. In general, the silica support comprises predominantly (i.e., at least 50% by weight) silica, with the optional addition of other components such as other inorganic refractory metal oxides (e.g., alumina, zirconia, titania, boria, thoria, ceria) and/or catalyst promoters or modifiers (e.g., alkali or alkaline earth metals, or transition metals in addition to tungsten). Typically, the support comprises silica in an amount of at least about 90% (e.g., from about 90% to about 100%) by weight and often at least about 95% (e.g., from about 95% to about 100%) by weight.

Types of silica for use as a component of, or otherwise for all or substantially all of, the silica support include amorphous silicas. Examples include Davisil®646, Davisil®636 (W.R. Grace & Co., Columbia, Md.) and other precipitated silicas. Regardless of the source, the silica will have a surface area, either as received or after an optional acid washing step in the catalyst preparation procedure, of at least about 250 square meters per gram (m$^2$/g), with particularly advantageous results being obtained in the range from about 250 m$^2$/g to about 600 m$^2$/g, and often from about 400 m$^2$/g to about 550 m$^2$/g. The average pore diameter of the silica, either as received or after acid washing, is preferably at least about 40 angstoms (Å), with exemplary average pore diameters being in the range from about 45 Å to about 170 Å, and even in the range from about 45 Å to about 100 Å. Surface area and average pore diameter are measured according to the Brunauer, Emmett and Teller (BET) method based on nitrogen adsorption (ASTM D1993-03 (2008)). As discussed above, it is thought that the combination of surface area and average pore diameter characteristics act in synergy, in the catalysts for olefin metathesis as described herein, to provide highly effective kinetic and size selective properties that simultaneously benefit both conversion and product selectivity.

Crystalline silicas may also be used in the silica support, with mesoporous materials such as MCM-41 being representative. Exemplary crystalline silicas have a silica to alumina molar ratio of at least about 1,000 corresponding to an atomic silicon to aluminum ratio (Si:Al ratio) of at least about 500. Typically, such siliceous materials used in the silica support have a silica to alumina molar ratio of at least about 3,000 (e.g., from about 3,000 to about 15,000), and often at least about 5,000 (e.g., from about 5,000 to about 10,000).

The silica support and consequently the catalyst itself can have a number of possible physical forms, with the specific form usually depending principally on the particular reaction system used. The support may be, for example, in the form of a powder that is sized to a desired average particle size, for example from about 35 mesh (0.50 mm) to about 60 mesh (0.25 mm). In reaction systems where a powder form would lead to an undesirably high pressure drop, larger spheres or extrudates (e.g., in the form of elongated cylinders) are commonly employed, with the specific shape being determined by factors such as pressure drop, mobility, diffusional distance, etc. In representative embodiments, the support has an average particle size, based on a representative dimension of the particle form (e.g., the diameter of a spherical form or the diameter of the circular cross section of a cylindrical, extruded form) from about 0.1 mm to about 5 mm.

In the preparation of catalysts for olefin metathesis, a support comprising silica having the properties described herein is impregnated with a tungsten compound to provide a tungsten impregnated silica support. Impregnation generally involves contacting the support with an impregnation solution of the tungsten compound. Suitable compounds include ammonium tungstate compounds such as ammonium metatungstate (AMT) and ammonium paratungstate (APT). The concentration of the tungsten compound in such impregnation solutions generally ranges from about 0.1 M to about 5 M. Static or flowing conditions may be used for contacting between the impregnation solution and silica support to effect the desired degree of tungsten impregnation. The impregnation solution contacting temperature is generally in the ranges from about 20° C. (68° F.) to about 200° C. (392° F.), and often from about 25° C. (77° F.) to about 150° C. (302° F.). The duration of contacting at this temperature (or contacting time) is generally from about 1 minute to about 5 hours, and often from about 5 minutes to about 3 hours. The contacting time is inclusive of any subsequent drying step, in which the support and impregnation solution remain in contact at a temperature within these ranges. The impregnation conditions are selected to achieve a desired level of tungsten (as tungsten metal), for example from about 1% to about 10% by weight, in the resulting catalyst.

Following impregnation, the tungsten impregnated support is then calcined to convert the tungsten compound to tungsten oxide ($WO_3$) that is a stable form of the tungsten prior to use, for example, in olefin metathesis. Calcining procedures that are effective for converting all or substantially all of the tungsten compound to $WO_3$ generally involve heating the support after impregnation to a temperature from about 300° C. (572° F.) to about 750° C. (1382° F.), and often from about 400° C. (752° F.) to about 650° C. (1202° F.), for a time (or duration of heating or the support to this temperature) generally from about 1 hour to about 10 hours, and often from about 3 hours to about 9 hours. The heating is normally performed with a flow of oxygen-containing gas (e.g., air, oxygen, or oxygen-enriched air). Usually during the catalyst preparation procedure, drying of the impregnated silica support is performed after the impregnation and before calcining of the tungsten impregnated silica support. Typical conditions for this drying step, if used, include a temperature from about 25° C. (77° F.) to about 250° C. (482° F.) and a time from about 0.5 hours to about 24 hours. The drying and/or calcining steps may be performed under purge with a gas (e.g., air, oxygen, nitrogen, argon, etc. or mixture of gases), preferably at ambient or slightly elevated pressure.

After calcination, it is possible to convert the tungsten oxide to other tungsten forms, for example by partial or complete reduction in the presence of flowing hydrogen, which may be more desirable within the reaction environment for catalyzing a particular reaction. The conversion may occur, for example, shortly prior to use and even in situ as a catalyst pretreatment. Therefore, while the catalyst may be prepared with the tungsten as tungsten oxide on a support comprising silica, it is not necessary that the tungsten oxide form be conserved in the reaction environment.

Optionally, acid washing of the silica support having the properties described herein and found to result in significant advantages with respect to tungsten catalysts for olefin metathesis, may be carried out prior to impregnation with the tungsten compound. Acid washing involves contacting the silica used in the support with an acid, including an organic acid or an inorganic acid. Particular inorganic acids include nitric acid, sulfuric acid, and hydrochloric acid, with nitric acid and hydrochloric acid being preferred. The acid concentration in aqueous solution, used for the acid washing, is generally in the range from about 0.05 molar (M) to about 3 M, and often from about 0.1 M to about 1 M. The acid washing can be performed under static conditions (e.g., batch) or flowing conditions (e.g., once-through, recycle, or with a combined flow of make-up and recycle solution).

Representative contacting conditions used to provide an acid washed silica support include a temperature generally from about 20° C. (68° F.) to about 120° C. (248° F.), typically from about 30° C. (86° F.) to about 100° C. (212° F.), and often from about 50° C. (122° F.) to about 90° C. (194° F.). The contacting time, or a duration over which the silica support is contacted with the acid at a temperature within any of these ranges, is generally from about from about 10 minutes to about 5 hours, and often from about 30 minutes to about 3 hours. Normally, it is preferred that the conditions of contacting used to perform acid washing of the silica support result in one or more observed physical or compositional changes in the support that can be verified analytically. For example, it has been determined that effective acid washing is generally accompanied by an increase in the surface area (BET method as indicated above) of the silica support of at least 5% (e.g., from about 5% to about 20%), and often at least 10% (e.g., from about 10% to about 15%), relative to the surface area of the support prior to being acid washed. Another change is a decrease in the amount of aluminum (as aluminum metal) of the acid washed support, relative to the amount in the support prior to being acid washed. The reduction in aluminum can be verified using inductively coupled plasma (ICP) techniques, known in the art, for the determination of trace metals. Generally, the amount of aluminum is decreased by at least about 35% (e.g., from about 35% to about 90%) and often at least about 50% (e.g., from about 50% to about 80%). A third change is a decrease in the average pore diameter of the acid washed silica support, relative to the average pore diameter of the support prior to being acid washed. In general, the pore volume is decreased by at least about 5%, and often by at least about 10%.

Overall aspects of the invention are directed to catalysts, and associated olefin metathesis processes, that exploit the significant benefits associated supports comprising silica having a surface area from about 250 $m^2/g$ to about 600 $m^2/g$ and an average pore diameter from about 45 Å to about 170 Å. Those having skill in the art, with the knowledge gained from the present disclosure, will recognize that various changes can be made in the above catalysts, processes using the catalysts, and methods of making the catalysts, without departing from the scope of the present disclosure.

The following examples are representative of the present invention and its associated advantages and are not to be construed as limiting the scope of the invention as set forth in the appended claims.

EXAMPLE 1

Characterization of Silica Supports

Samples of 6 different silicas were obtained as silica powders from commercial sources. These silicas were the mesoporous molecular sieve MCM-41 (Mobil Composition of Matter No. 41, available from Sigma-Aldrich, Inc., St. Louis, Mo., USA) and the precipitated silicas (available from W.R. Grace & Co., Columbia, Md.) having the tradenames Davisil®12, Davisil®923, Davisil®636, Davisil®646, and Grace XWP-Gel-P005 (extra wide pore silica). The silica samples were analyzed for surface area and average pore diameter using the BET method described above, and this analysis revealed a wide range in both parameters for commercial silica samples, as shown below in Table 1.

TABLE 1

Surface Areas and Average Pore Diameters of Silicas

|  | Davisil® 923 | Davisil® 636 | Davisil® 646 | XWP-Gel-P005 | Davisil® 12 | MCM-41 |
|---|---|---|---|---|---|---|
| BET Surface Area, $m^2/g$ | 484 | 451 | 293 | 80 | 691 | 974 |
| Pore Diameter, Å | 32 | 78 | 166 | 430 | 23 | 36 |

EXAMPLE 2

Tungsten Impregnation of Silica Supports and Calcination

Each of the 6 different silica samples described in Example 1, sized to 35-60 US mesh (0.25-0.5 mm), was impregnated with tungsten. The impregnation was performed at varying targeted tungsten levels, namely 1.5%, 4%, 6.5%, and 9% (as tungsten metal) based on the total dry catalyst weight. To perform the impregnation, the supports were weighed into 12 crucibles using about 1-2 ml per crucible well. Weighing was performed either manually or otherwise using an automated powder dispensing system. The tungsten was added, in the form of an ammonium metatungstate solution, to separate empty crucibles. Liquid reagent was pipetted and diluted with deionized water, to obtain about a 2:1 solution to silica ratio, using the Zinsser Lissy® GXL liquid handling system. The solids were then added to the corresponding liquids. The mixtures were placed on a vortexer for 10 minutes and then rotary dried under 2 psig flowing nitrogen at 120° C. (248° F.) for 1-2 hours, until free flowing. The dried, tungsten impregnated silica supports were then calcined in a muffle oven under low pressure air flow for one hour at 100° C. (212° F.) and three hours at 500° C. (932° F.). The resulting tungsten oxide catalysts on silica supports were then evaluated for their performance in the metathesis of ethylene and butylene to produce propylene, as described below in Example 3.

EXAMPLE 3

Evaluation of Tungsten Oxide Catalysts

The $WO_3$ catalysts prepared in Example 2 were evaluated for metathesis of an ethylene and butylene feedstock to produce propylene in a high-throughput experimental protocol. Samples of the catalysts, 200 microliter (µl) each, were tested in a microreactor array system (High Pressure Reactor Assay Module from Sintef (Trondheim, Norway)) equipped with a gas and liquid flow control module, reactor/oven assembly, and analytical section providing 48 individual reactor channels. The catalysts were reduced for 45 minutes at 500° C. (932° F.) under flowing hydrogen, using a temperature ramp rate of 2° C. (4° F.) per minute. The tests were performed at catalyst bed temperatures of 343° C. (649° F.), 400° C. (752° F.), 425° C. (797° F.), and 343° C. (649° F.), respectively. The four temperature conditions were evaluated consecutively over durations of 4, 4, 6, and 4 hours, respectively.

A hydrocarbon feedstock of ethylene and butylene at an ethylene:butylene target molar ratio of 1.5 was supplied from cylinders, with the ethylene meeting ultra high purity (UHP) specifications and the butylene being technical grade material containing about 93-95 mole-% cis and trans 2-butenes. The liquid hourly space velocity (LHSV), or volumetric flow rate of the hydrocarbon feedstock divided by the catalyst bed volume, was controlled at 0.9 $hr^{-1}$. Also, the reactor pressure set point was maintained at a target value of 32 barg (465 psig) throughout the olefin metathesis testing.

The reactor effluent composition was analyzed periodically using a high-speed gas chromatography method developed to accommodate the high-throughput experimentation. The analytical results were used to determine both the conversion level (per pass), based on the total percentage conversion of feed carbon, and the selectivity, based on the total percentage of converted carbon that resulted in the formation of propylene. Average propylene selectivity and feed conversion values (per pass) were calculated over the duration of each temperature condition used for olefin metathesis performance evaluation. The propylene yield (per pass) was calculated as the product of conversion and selectivity.

Figure 1:
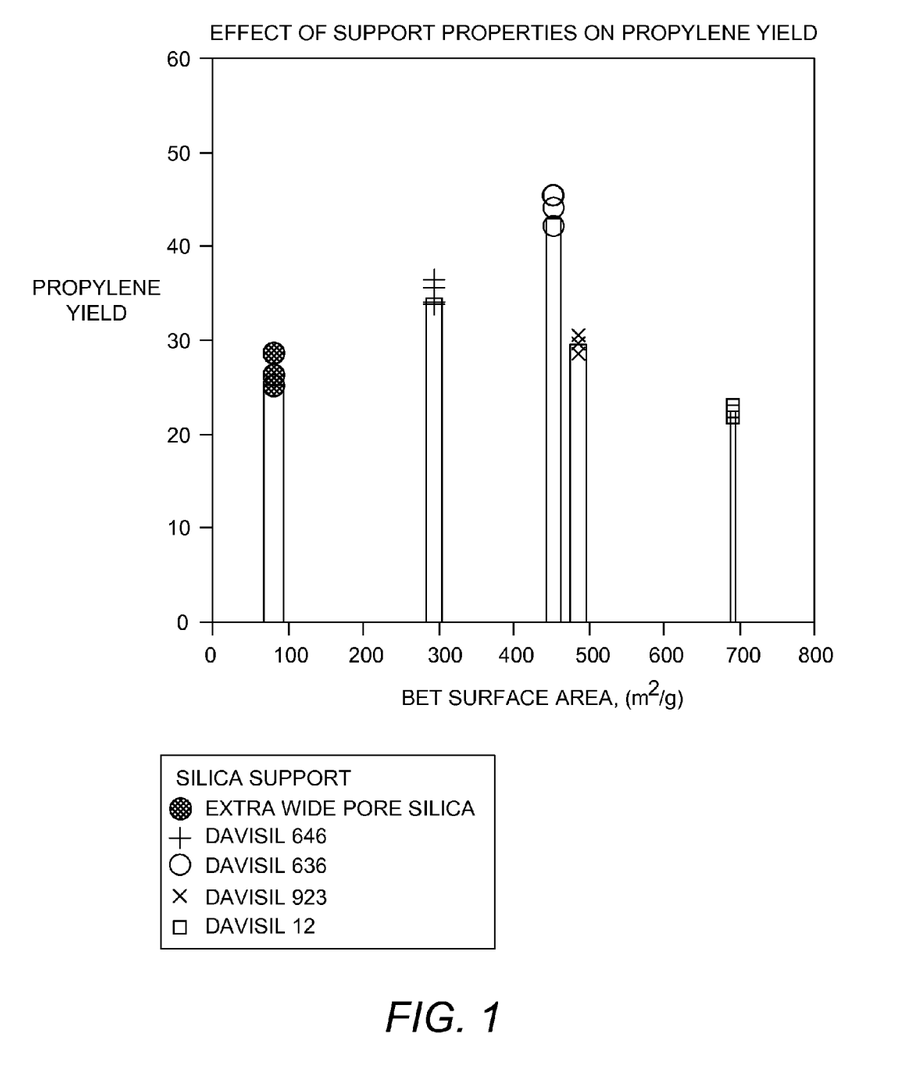
FIG. 1 graphically depicts the propylene yield obtained from the metathesis of ethylene and butylene at constant process conditions, in the presence of catalysts comprising tungsten disposed on silica supports, as a function of the surface area of the silica used in the supports.

FIG. 1 shows the propylene yield, at 425° C. (797° F.) reactor temperature, obtained from the olefin metathesis evaluation, as a function of the BET surface area of the silica used in the catalyst supports. The other process conditions were as described above. The five catalysts compared in this figure had a target 6.5 wt-% tungsten loading on Davisil®12, Davisil®923, Davisil®636, Davisil®646, and Grace XWP-Gel-P005 (extra wide pore silica). The results show that significant and commercially important advantages in terms of propylene yield are obtained for supports comprising silica having a BET surface area of about 450 $m^2/g$ and more broadly in the range from about 250 $m^2/g$ to about 600 $m^2/g$.

Figure 2:
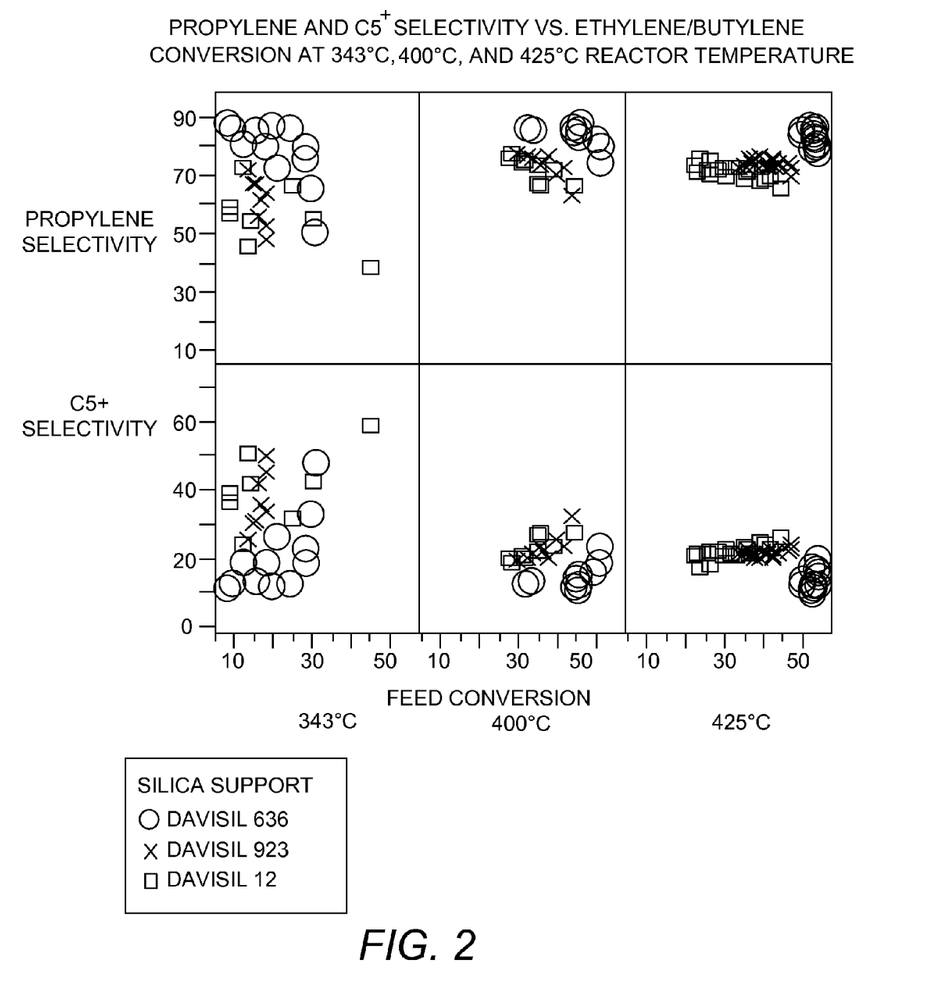
FIG. 2 graphically depicts product selectivity as a function of ethylene and butylene conversion, at three different catalyst bed temperatures, namely 343° C. (649° F.), 400° C. (752° F.), and 425° C. (797° F.), in the production of propylene from ethylene and butylene by olefin metathesis in the presence of catalysts comprising tungsten disposed on silica supports. The selectivity of the main product, propylene, as well as the 5-carbon number and higher byproducts ($C_5^+$) are both shown, as obtained using catalysts having supports containing silica with 3 different average pore sizes.

FIG. 2 shows the propylene selectivity, as well as the $C_5^+$ hydrocarbon byproduct selectivity, as a function of conversion obtained from the olefin metathesis evaluation at the three different catalyst bed temperatures, namely 343° C. (649° F.), 400° C. (752° F.), and 425° C. (797° F.). The other process conditions were as described above. The three catalysts compared in this figure had a target 6.5 wt-% tungsten loading on Davisil®12, Davisil®923, and Davisil®636. The results show that the catalyst supported on Davisil®636 had not only increased activity (conversion level at a given temperature) but also increased propylene selectivity and decreased $C_5^+$ selectivity, compared to catalysts having supports comprising silica with other surface area/average pore diameter characteristics. While the Davisil® 923 silica had a surface area in the range from about 250 $m^2/g$ to about 600 $m^2/g$, the average pore diameter of the silica was below the range of 45 Å to 170 Å, as discussed above. Davisil®12 did not have a surface area or average pore diameter within these desired ranges.

Figure 3:
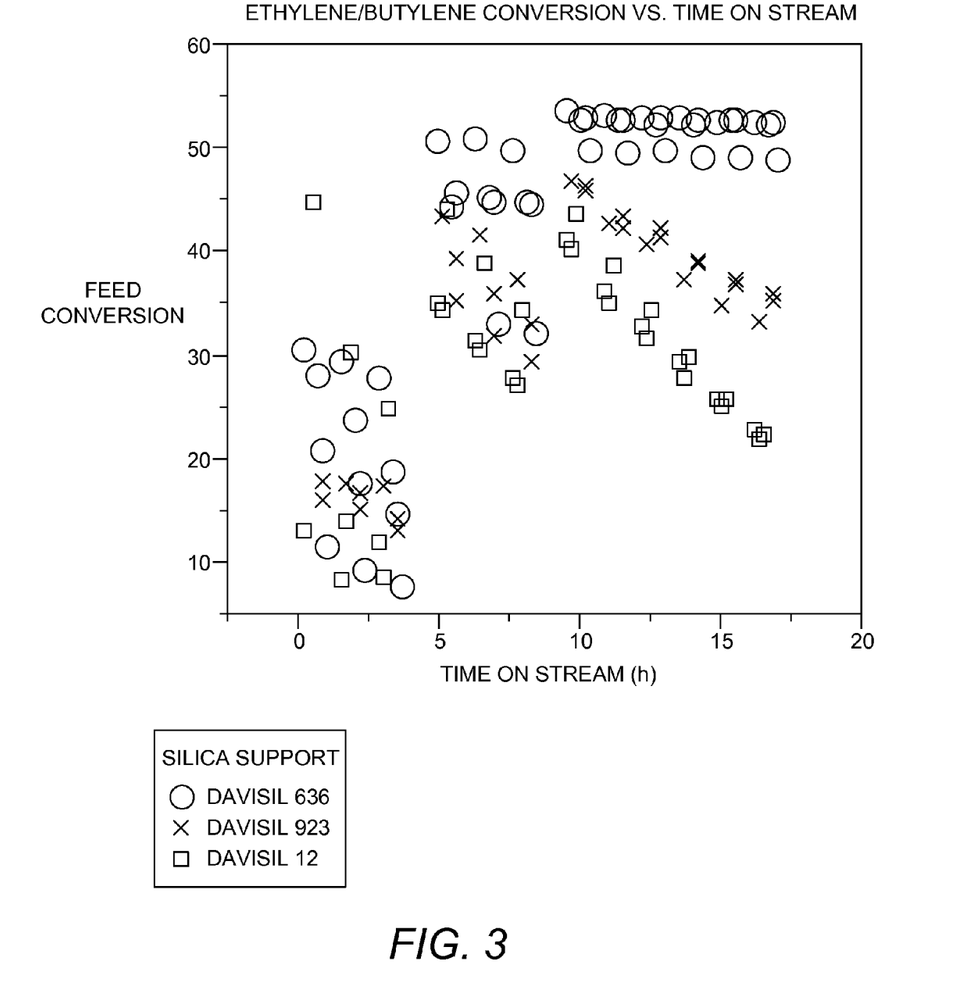
FIG. 3 graphically depicts conversion of ethylene and propylene as a function of time on stream in the production of propylene from ethylene and butylene by olefin metathesis in the presence of catalysts comprising tungsten disposed on silica supports. The conversion data were obtained using catalysts having supports containing silica with 3 different average pore sizes.

FIG. 3 shows conversion, at 425° C. (797° F.) catalyst bed temperature as a function of time on stream, obtained from the olefin metathesis evaluation. The other process conditions were as described above. The conversion data were obtained using catalysts having supports containing silica with 3 different average pore sizes. The three catalysts compared in this figure had a target 6.5 wt-% tungsten loading on Davisil®12, Davisil®923, and Davisil®636. Again, the results show the superiority in performance of the catalyst supported on Davisil®636, compared to catalysts having supports comprising silica with other surface area/average pore diameter characteristics.

Figure 4:
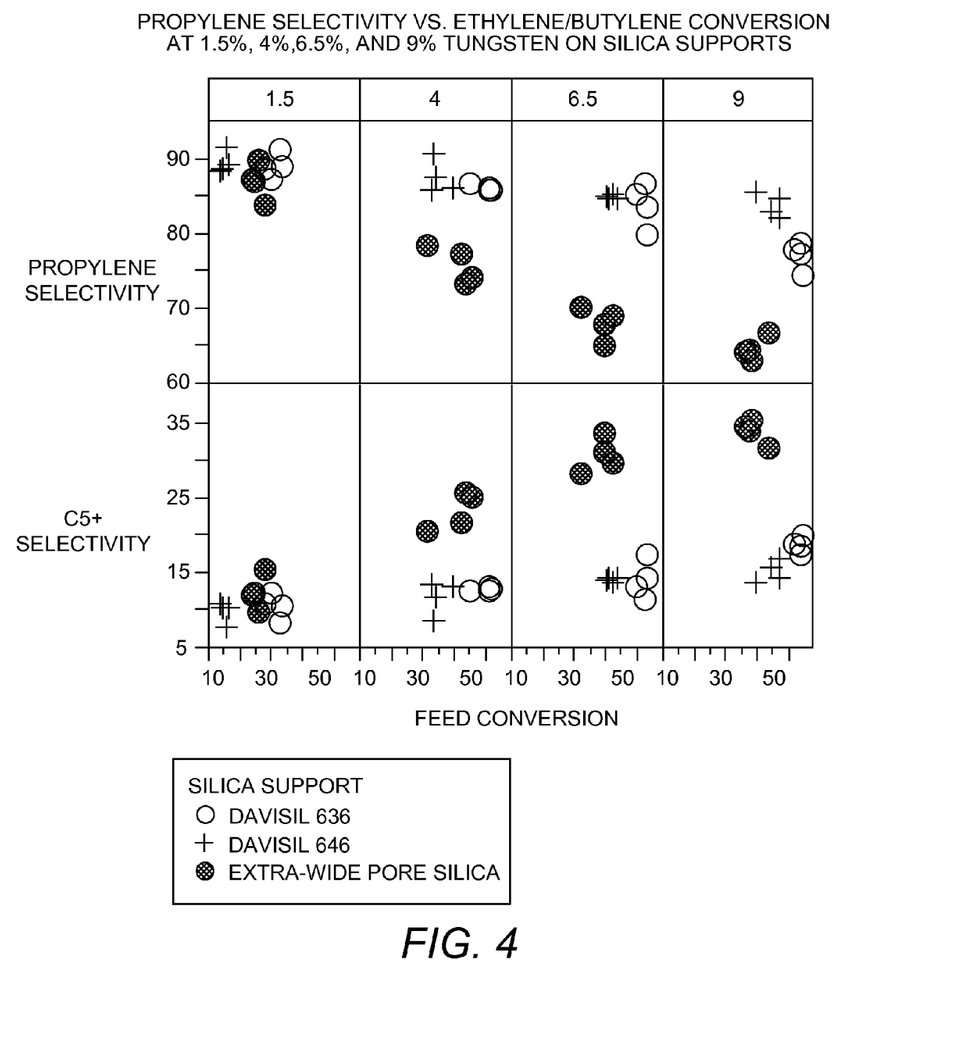
FIG. 4 graphically depicts product selectivity as a function of ethylene and butylene conversion, in the production of propylene from ethylene and butylene by olefin metathesis in the presence of catalysts comprising tungsten, at four different tungsten levels, namely 1.5%, 4%, 6.5%, and 9%, disposed on silica supports. The selectivity of the main product, propylene, as well as the 5-carbon number and higher byproducts ($C_5^+$) are both shown, as obtained using catalysts having supports containing silica with 3 different average pore sizes.

FIG. 4 shows the propylene selectivity, as well as the $C_5^+$ hydrocarbon byproduct selectivity, as a function of conversion obtained from the olefin metathesis evaluation at 425° C. (797° F.) catalyst bed temperature. The other process conditions were as described above. The catalysts compared in this figure had target tungsten loadings of 1.5 wt-%, 4 wt-%, 6.5 wt-%, and 9 wt-% on three different silica types, namely Davisil®636, Davisil®646, and Grace XWP-Gel-P005 (extra wide pore silica). The results show the superiority in conversion and/or selectivity of the catalyst supported on Davisil®636 or Davisil®646 silica, compared to catalysts having supports comprising silica with other surface area/average pore diameter characteristics. XWP-Gel-P005 (extra wide pore silica) did not have a surface area or average pore diameter within the desired ranges discussed above.

The above results illustrate that $WO_3$ catalysts having supports comprising silica with the surface area/average pore diameter characteristics described herein, provide exceptional performance in olefin metathesis.

The invention claimed is:

1. A method for preparing a catalyst comprising tungsten oxide disposed on a support comprising silica, the method comprising:

(a) impregnating a support comprising silica having a surface area from 400 m²/g to 550 m²/g with a tungsten compound to provide a tungsten impregnated silica support;
(b) calcining the tungsten impregnated silica support to provide the catalyst ; and
(c) acid washing the silica support before impregnating the silica support with the tungsten compound to increase the surface area of the silica support by at least 5%, and wherein the acid used in acid washing is selected from the group consisting of nitric acid and hydrochloric acid; wherein the catalyst is for use in olefin metathesis.

2. The method of claim 1, wherein the support has an average particle size from about 0.1 mm to about 5 mm.

3. The method of claim 1, further comprising, after impregnating step (a), drying the tungsten impregnated silica support at a temperature from about 25° C. (77° F.) to about 250° C. (482° F.) for a time from about 0.5 hours to about 24 hours.

4. The method of claim 1, wherein the calcining step (b) is carried out at a temperature from about 300° C. (572° F.) to about 750° C. (1382° F.) for a time from about 1 hour to about 10 hours.

5. The method of claim 1, wherein the tungsten compound is an ammonium tungstate compound.

* * * * *